US00PP28079P3

(12) United States Plant Patent
Byrne et al.

(10) Patent No.: US PP28,079 P3
(45) Date of Patent: Jun. 6, 2017

(54) PEACH TREE NAMED 'ROYAL ZEST FOUR'

(50) Latin Name: *Prunus persica*
Varietal Denomination: ROYAL ZEST FOUR

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 81 days.

(21) Appl. No.: 14/544,515

(22) Filed: Jan. 13, 2015

(65) Prior Publication Data

US 2016/0205839 P1 Jul. 14, 2016

(51) Int. Cl.
*A01H 5/08* (2006.01)

(52) U.S. Cl.
USPC ..... Plt./198

(58) Field of Classification Search
USPC ..... Plt./198
See application file for complete search history.

(56) References Cited

U.S. PATENT DOCUMENTS

PP7,290 P 8/1990 Zaiger et al.

OTHER PUBLICATIONS

"Royal and Golden Zest Peaches," Texas A&M AgriLIFE, Feb. 8, 2013.*
The Brooks and Olmo Register of Fruit and Nut Varieties, 3rd Ed., American Society of Horticultural Science Press, Alexandria, VA, 1997.
Brooks, R. M. 1958. Double Delight, Earligold, and June Gold peaches. Fruit Var. J. 3:22.
Okie, W. R. 1993. 'Goldprince' and 'Scarletpearl' peaches. HortScience 28:231.
Rouse, R. and W. Sherman. 1989. 'TropicBeauty': a low-chilling peach for subtropical climates. HortScience 24:165-166.

* cited by examiner

*Primary Examiner* — Anne Grunberg
(74) *Attorney, Agent, or Firm* — Ramey & Schwaller, LLP

(57) ABSTRACT

Disclosed is a new variety of *Prunus persica* named 'ROYAL ZEST FOUR'. This new variety, which requires approximately 550 chilling units of dormancy, is considered to be a peach tree of mid season maturity, which produces yellow fleshed fruit that are firm, attractively colored, and suitable for both local and regional markets.

4 Drawing Sheets

BACKGROUND OF THE INVENTION

Field of the Invention

This invention relates to peach trees and, more specifically, to peach trees referred to as a variety of *Prunus persica* named 'ROYAL ZEST FOUR'. 'ROYAL ZEST FOUR', which requires approximately 550 chilling units of dormancy, produces an exceptionally high quality, firm semi-freestone peach that matures in early to mid-June in the medium chill zone of Texas.

SUMMARY OF THE INVENTION

The 'ROYAL ZEST FOUR' peach is characterized as to novelty and is otherwise noteworthy by producing fruit that ripens in the early midseason; is considered high quality; and which is firm and has an attractive coloration. In this regard, the present variety of peach tree bears fruit that are ripe for commercial harvesting and shipment in the early to mid-June, when the fruit is grown in the medium chill zone of Texas.

ORIGIN OF THE VARIETY

The present peach tree was the result of an ongoing Stone Fruit Breeding Program of Texas A & M University, College Station, Brazos County, Tex. To this end, controlled crosses are made each year in order to produce seedling populations from which improved progenies are evaluated and selected.

The seedling 'ROYAL ZEST FOUR' (TX4E169) was originated at the Texas A & M University Horticultural Farm in College Station, Tex. in 2000, and was chosen from a population of seedlings that resulted from seed from a cross between the yellow-fleshed California peach 'Rich Lady' (U.S. Plant Pat. No. 7,290) as the female parent and the early ripening, medium chill peach, 'Victor' (UPOV PBR PRUNU PER grant #25391) as the male or pollen parent. 'Victor' was released by Texas A&M University for use in Spain and is a seedling from the cross between the low chill, yellow-fleshed, mid-season cultivar 'Tropic Beauty' (not patented) and the early ripening, yellow-fleshed, medium chill peach 'Goldprince' (not patented). 'Tropic Beauty' was jointly released by the University of Florida and Texas A&M University (Rouse and Sherman, 1989) and is derived from a cross between a Florida selection Fla3-2 (K6E121open pollinated) (not patented) as the female parent and 'Flordaprince' (Fla2-7×'Maravilha') (not patented) as the male parent. 'Goldprince' was released by the USDA breeding program in Byron, Ga. (Okie, 1993) and is derived from a cross between 'Loring' (not patented) as the female parent and the Georgia unreleased selection FV3-257 (not patented) as the male parent. Resulting seed from this cross were planted in 1998 at the Texas A & M University Horticultural Farm in College Station, Tex. 'ROYAL ZEST FOUR' was marked as TX4E169 for subsequent observation and noted as having exceptional characteristics. Two-year and older trees of the variety were subsequently evaluated during the 2005 through 2013 fruit growing seasons in both California (Fowler) and Texas (Terrell, Fairfield and College Station).

The new variety 'Royal Zest Four' differs from 'Rich Lady', its yellow-fleshed, high chill female parent as it requires less chilling (approximately 550 chill hours versus approximately 800 chill hours), blooms 4-9 days earlier, ripens 5-8 days earlier, and has a more rounded shape in the medium chill zone of Texas.

'Royal Zest Four' differs from 'Victor', its medium chill, yellow fleshed male parent as it requires more chilling accumulation to break dormancy (550 versus 400 chilling hours), blooms approximately 12 days later, and ripens approximately 4 weeks later.

ASEXUAL REPRODUCTION OF THE VARIETY

'ROYAL ZEST FOUR' was bud grafted onto virus-free Nemaguard (not patented, Brooks and Olmo, 1997) peach rootstock in June 1998 at the nursery site in Oakdale, Calif. The variety was subsequently planted at the experimental orchard in the central portion of the San Joaquin Valley, near Fowler, Fresno County, Calif. and in three sites in Texas (College Station, Fairfield and Terrell). Fruit from the resulting propagation has been evaluated during the period from 2005 to 2013 fruit seasons. This evaluation clearly demonstrated that the re-propagated trees were true to the characteristics of the original seedling in all observable aspects.

BRIEF DESCRIPTION OF THE DRAWINGS

This new variety of peach tree is illustrated by the accompanying photographs. The fruit, pits, flowers, and shoots depicted are from mature trees that are 5 years of age.

BOTANICAL DESCRIPTION OF THE VARIETY

Figure 1:
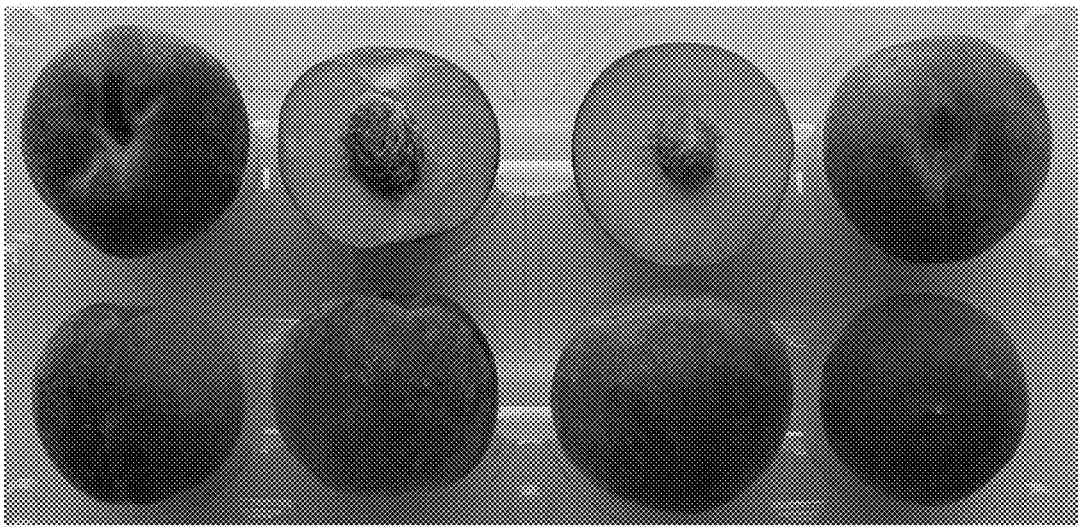
FIG. 1. Color picture showing the flesh and skin color and fruit shape of 'Royal Zest Four' produced in the medium chill zone of Texas (Fairfield).
Figure 2:
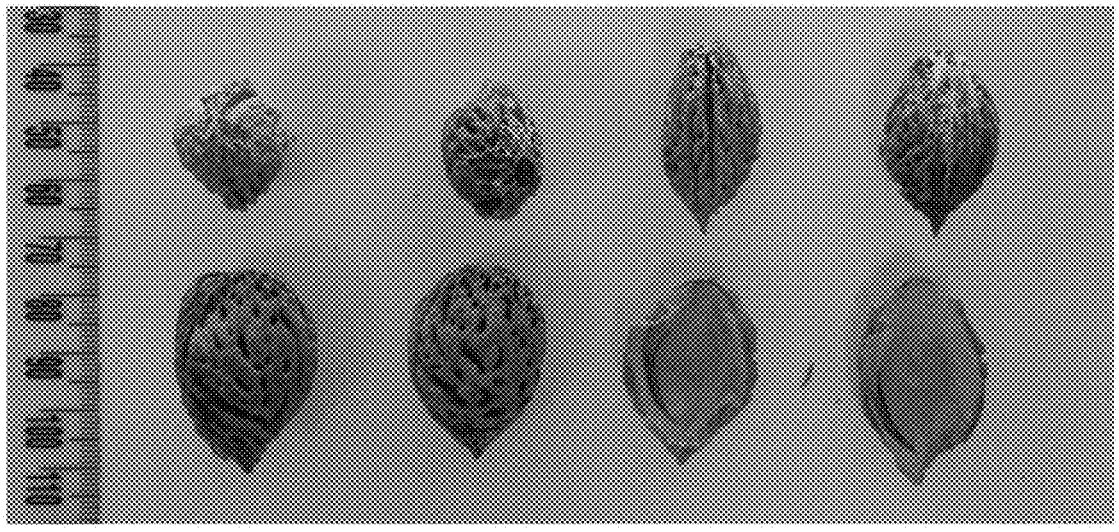
FIG. 2. Color photograph of the endocarp of 'Royal Zest Four'. The ruler is demarcated in millimeters.
Figure 3:
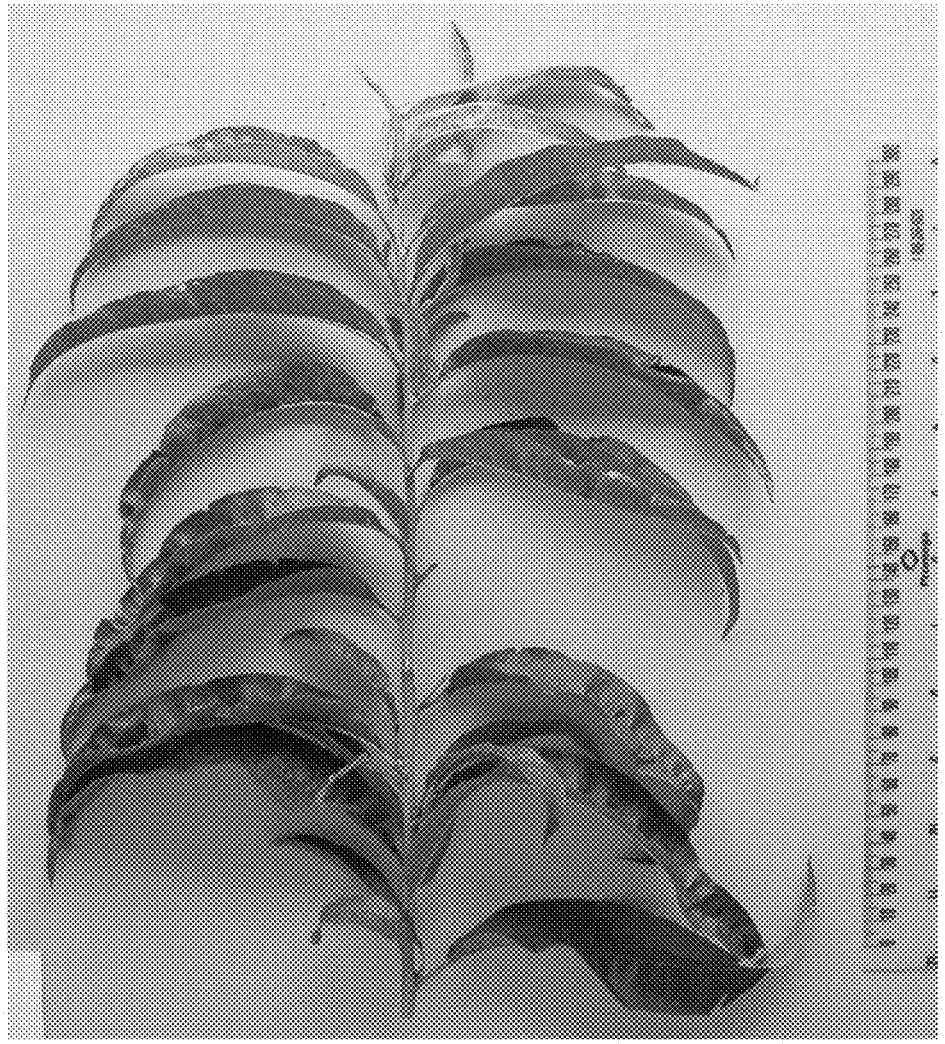
FIG. 3. A stem showing the leaves of the 'Royal Zest Four' peach. The ruler is demarcated in millimeters.
Figure 4:
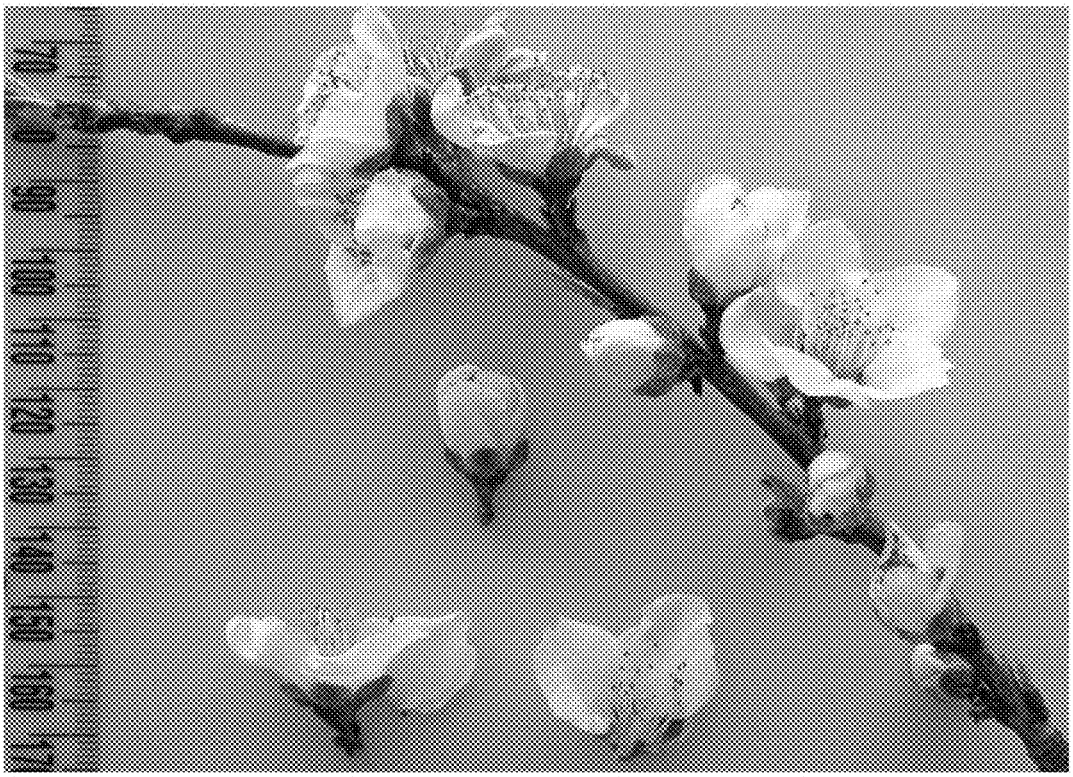
FIG. 4. The showy flowers of 'Royal Zest Four'. The ruler is demarcated in millimeters.

Referring more specifically to the pomological details of this new and distinct variety of peach tree, the following has been observed under the ecological conditions prevailing at the experimental orchards in the medium chill zone of Texas on mature 5-year old trees. All major color code designations are by reference to The R.H.S. Colour Chart (2001) provided by The Royal Horticultural Society of Great Britain. Colors are approximate as color depends on horticultural practices such as light level and fertilization rate, among others.

Tree:

*Size.*—Generally average to above average as compared to other common peach cultivars ripening in the mid-season of maturity.

*Height.*—7 feet (2.13 m) on five-year old trees pruned to an open center training system.

*Width.*—10 feet (3.05 m) at the end of the 2012 growing season on a 5-year old tree.

*Vigor.*—High.

*Density.*—Medium to high.

*Productivity.*—Productive.

*Shape.*—The trees are vigorous with the typical semi-spreading growth habit similar to 'TexKing' (U.S. Plant Pat. No. 14,627), 'TexPrince' (U.S. Plant Pat. No. 14,629), and 'TexRoyal' (not patented, Byrne and Bacon, 1991).

*Current season growth.*—The current season growth for the new variety was approximately 3.4 to 4.4 feet (1.0-1.3 m).

*Regularity of bearing.*—Regular, and considered hardy under typical conditions in the medium chill zone of Texas (USDA Hardiness zones 8a and 8b) and in the central San Joaquin Valley of California (USDA Hardiness 9b).

Trunk:

*Size.*—Approximately 4.5 inches (11.43 cm) in diameter and 18.0 inches (45.72 cm) in circumference when measured at a distance of approximately 12 inches (30.5 cm) above the soil level, at the end of the 2012 growing season on a five-year old tree.

*Bark texture.*—Considered moderately rough with numerous folds of papery scarf-like skin being present.

*Bark coloration.*—Variable, RHS colors present are N200D of the Brown Group, 201D of the Grey Group and 202D of the Black Group.

Branches:

*Size.*—Considered medium for the variety.

*Thickness.*—Average (about 6.2 cm in diameter as measured 10 cm from the trunk on a five-year old tree) as compared to other varieties.

*Surface texture.*—Average and appearing furrowed on wood that is several years old.

*Lenticels.*—Numerous flat, oval lenticels present. The lenticels range in size from approximately 5 to 7 mm in width and were approximately 1 mm in height.

*Current season shoots.*—Surface texture — Substantially glabrous.

*Internode length.*—Approximately 1.0 to 4.5 cm as measured in the middle of a current season stem.

*Color of mature branches.*—The predominant colors are 176A-B and 177A of the Greyed-Orange Group, 198D of the Greyed-Green Group and N200C-D of the Brown Group.

*Current season shoots.*—Color — Light green (142A-B and 143C of the Green Groups) with some reddish-brown coloration appearing on exposed surface of the shoots (164A of the Greyed-Orange Group). The color of new shoot tips is considered a bright and shiny green (mainly 149B-C of the Yellow-Green Group).

*Type of bearing.*—Long shoots only.

*Spur length.*—Not applicable.

*Vegetative bud size.*—Generally 2-4 mm in length on the mid-portion of a late summer shoot.

*Vegetative bud shape of apex.*—Acute.

*Position of vegetative bud in relation to one-year old shoot.*—Slightly held out.

Leaves:

*Size.*—Considered medium for the species. Leaf measurements have been taken from vigorous upright current season growth approximately at mid-shoot.

*Leaf length.*—Approximately 141 to 170 mm.

*Leaf width.*—Approximately 37 to 38 mm.

*Leaf thickness.*—Less than 1 mm.

*Leaf form.*—Lanceolate.

*Leaf tip form.*—Acuminate.

*Leaf upper surface color.*—Green, approximately 137A-B of the Green Group.

*Leaf lower surface color.*—Green, approximately 146A-D and 1478 of the Yellow-Green Group.

*Leaf mid-vein color.*—Light green, approximately 145C of the Yellow-Green Group.

*Leaf margins.*—

*Form.*—Considered crenate/crenulate.

*Uniformity.*—Considered generally uniform.

*Leaf petioles.*—

*Size.*—Considered medium long.

*Length.*—Approximately 12 to 14 mm.

*Thickness.*—Approximately 1 to 1 5 mm.

*Color.*—Pale green (145C of the Yellow-Green Group).

*Leaf glands (nectaries).*—

*Size.*—Approximately 2-4 mm in height and 1 mm in width.

*Number.*—Generally 2 per leaf.

*Type.*—Reniform.

*Color.*—Light to medium brown (177B-C of the Greyed-Orange Group and 200C-D of the Brown Group).

*Position.*—Predominantly on the base of the leaf blade.

*Leaf stipules.*—

*Size.*—Medium for the species.

*Length.*—Approximately 10 to 12 mm.

*Form.*—Lanceolate.

*Color.*—Green (144B-C of the Yellow-Green Group) with reddish brown tips (approximately 165B Greyed-Orange Group) when young. The stipules are considered to be early deciduous.

*Ratio of wood (leaf) buds to flowering buds.*—1 to 2 flower buds per vegetative bud.

Flowers:

*Floral buds.*—

*General.*—The floral buds are considered to be medium in size, conic in form, and slightly appressed relative to the bearing shoot.

*Color.*—The bud scales are gray-brown, (approximately Greyed-Purple Group 187A-B and Brown Group 200A-B). The buds are considered hardy under the typical climatic conditions of the medium chill zone of Texas and the central San Joaquin Valley, Calif.

*Length.*—Approximately 4 to 6 mm.

*Blooming type.*—Considered early in relation to other peach cultivars commonly growing in the medium chill zone of Texas. Date of full bloom was between February 28$^{th}$ and March 10$^{th}$ during the period between 2006 and 2011. The mean flowering time was about the 2$^{nd}$ of March, 7-9 days before flowering of 'June Gold' (U.S. Plant Pat. No. 1,884).

*Flower fertility.*—Self-fertile.

*Flower type.*—Showy.

*Flower size.*—Flower diameter at full bloom is approximately 30 to 38 mm.

*Bloom quantity.*—Considered abundant.

*Flower bud frequency.*—Normally 1 to 2 per node.

*Petal size.*—

*General.*—Considered medium to medium large for the species.

*Width.*—Approximately 13 to 16 mm.

*Length.*—Approximately 15 to 19 mm.

*Petal form.*—Broadly ovate.

*Petal count.*—Nearly always 5.

*Petal color.*—Medium pink when young (Red-Purple Group 62B-D and 65B), becoming darker near the petal claw.

*Flower arrangement of petals.*—Overlapping to touching when the flower is partially to fully open.

*Petal claw.*—

*Form.*—The claw is present and has a medium size when compared to other varieties.

*Length.*—Approximately 1 to 2 mm.

*Width.*—Approximately 1 mm.

*Petal margins.*—Generally considered variable, from nearly smooth to slightly undulate.

*Petal apex.*—Generally — The petal apices appear slightly domed.

*Flower pedicel.*—

*Length.*—Considered long, and having an average length of approximately 3 to 4 mm.

*Thickness.*—Considered average, approximately 1 mm.

*Color.*—Light green (Yellow-Green Group 144C-D, N144B-D and 145A-B).

*Floral nectaries.*—

*Color.*—Dull to bright orange (Yellow-Orange Group 23A-B, Orange Group 24A, 25A-B and N25A-B).

*Hypanthium.*—

*Surface texture.*—Generally glabrous.

*Color.*—A brownish red with an underlayment of green (approximately Yellow-Green Group 144C-D, N144B-D, 145A-B, Greyed-Purple Group 183A-C and 185C).

*Sepals.*—

*Surface texture.*—The surface has a short, fine, wooly and a gray-colored texture.

*Size.*—Average, and ovate in form.

*Color.*—A brownish red with an underlayment of green (approximately Yellow-Green Group 144C-D, N144B-D, 145A-B, Greyed-Purple Group 183A-C and 185C).

*Anthers.*—

*General.*—Average in size for the species.

*Color.*—Medium yellow with red (approximately Yellow Group 7B-D, Red Group 42A-B, 45A-C and 46A-B).

*Pollen production.*—Pollen is abundant, and is a yellow color.

*Filaments.*—

*Size.*—Variable in length, approximately 12 to 14 mm, with the filaments equal to or slightly longer than the pistil.

Color.—White with light pink when young (approximately Red-Purple Group 62D, 65C-D, White Group 155A-D and N155B-C) and darkening to very dark pink (Red-Purple Group 71B, 72C-D and N74C-D) with advanced maturity.

*Anther position relative to pistil and petals.*—Anthers generally at the same height or higher than the pistils.

The anthers do not protrude when the flower is at the pink bud stage of development.

*Pistil.*—

*General.*—Average in size, but slightly shorter or equal to the general anther height, overall.

*Length.*—Approximately 16 to 17 mm, including the ovary.

*Color.*—Considered a very light yellow-green when young (Green-Yellow Group 1B-D), and developing a reddish hew with advancing senescence (Red-Purple Group 59D, 60D and 61C).

*Surface texture.*—The variety has a long, silver white pubescent pistil (approximately White Group 155A-D).

Fruit:

*Maturity.*—The present variety of fruit is described, as it would be found in its firm ripe condition at full commercial maturity. Under the ecological conditions prevailing in the medium chill zone of Texas. Over the period between 2006 and 2011 it ripen between June $5^{th}$ and June $22^{nd}$ with a mean first ripe date of June $16^{th}$ in the medium chill zone of Texas.

*Size.*—General — Medium to medium large for the season and considered uniform.

*Average cheek diameter.*—Approximately 61 to 65 mm.

*Average suture diameter.*—Approximately 64 to 65 mm.

*Average axial diameter.*—Approximately 56 to 60 mm.

*Fruit form.*—Generally round with unequal halves. Occasionally the fruit exhibits less symmetry when comparing the suture height with the line opposite the suture. The fruit is generally uniform in symmetry when viewed from the apical aspect.

*Fruit suture.*—Generally, the suture appears as a thin line that extends from the base to the apex, and appears deeper at the apex, forming a shallow basin at the apical point. The suture is even or within 2-4 mm of being even with the surrounding fruit surface.

*Color.*—The suture normally is the same color as the underlying blush (Red Group 53A).

*Ventral surface.*—Form — Considered uniform.

*Stem cavity.*—

*Size.*—Considered medium for the species.

*Width.*—Approximately 12 to 15 mm.

*Length.*—Approximately 25 to 26 mm.

*Depth.*—Approximately 12 to 13 mm.

*Fruit base.*—Flat.

*Fruit apex.*—Flat.

*Fruit stem.*—

*Generally.*—Considered medium to medium short in length, approximately 9 mm.

*Thickness.*—Approximately 5 mm.

*Color.*—Bright green (Green Group 142A).

*Fruit skin.*—Generally considered medium or average in thickness.

*Surface texture.*—Thick pubescence.

*Skin acidity.*—Considered neutral.

*Tenacious to flesh.*—Yes.

*Tendency to crack.*—Not observed.

*Skin color.*—Generally — Variable, with approximately 60-90% of the fruit surface covered with an attractive orange red blush as described below under Blush Color.

*Down.*—Thick and short.

*Blush color.*—The blush color is generally more prevailing apically. This red blush ranges from a medium, clear red (Red Group 45A) to dark red (Red Group 53A) with many degrees of shading and blending occurring between these colorations.

*Skin ground color.*—Light yellow (Yellow Group 2C).

*Flesh color.*—Medium orange-yellow (Yellow-Orange Group 16C).

*Flesh fibers.*—Present, numerous and lightly colored. These fibers are present throughout the flesh.

*Stone cavity flesh color.*—Medium orange-yellow (Yellow-Orange Group 14B).

*Flesh texture.*—Generally, the flesh is considered from and fine at commercial maturity.

*Ripening.*—Generally the fruit of the present variety ripens evenly.

*Flavor.*—Considered sweet with slightly acidic flavor.

*Soluble solids.*—Ranges from 10 to 15 Brix.

*Titratable acidity.*—Generally ranges from 8.0-11.1 meq H+/mL of juice depending on the ripeness of the fruit.

*Aroma.*—Pleasant and reasonably abundant.

*Eating.*—Generally considered very good to excellent.

Stone:

*Attachment.*—Freestone at commercial maturity.

*Stone size.*—Generally considered medium to medium-large relative to the ratio of stone to fruit size.

*Length.*—Approximately 31 to 35 mm.

*Width.*—Approximately 25 to 24 mm.

*Thickness.*—Approximately 16 to 19 mm.

*Fibers.*—Rarely a few medium length fibers are attached along the surface of the stone.

*Stone form.*—Ovate.

*Stone base angle.*—Wide.

*Apex shape.*—Medium.

*Stone shape.*—Considered variable, ranging from ovid to elongated.

*Stone surface.*—

*Surface texture.*—Minor surface markings are honeycombed with chains of pits.

*Ridges.*—Numerous fine ridges are present basally, and converge towards the base of the stone.

*Ventral edge.*—Small.

*Dorsal edge.*—Shape — Grooved and having moderately rough edges.

*Stone color.*—The color of the dry stone is a light brown-tan color (Greyed-Yellow Group 161C-D and Greyed-Orange Groups 164B-D and 165C-D). The color of the inside surface of the endocarp is primarily 159A of the Orange-White Group and 164B-C and 165C-D of the Greyed-Orange Group.

*Tendency to split.*—Splitting has not been observed.

*Kernel.*—The kernel fills the endocarp at harvest and measures approximately 4-5 mm in thickness, 9-10 mm in width, and 15-18 mm in length. When dried the shriveled kernels measure approximately 2-4 mm in thickness, 10-11 mm in width, and 16-17 mm in length. The colors of the shriveled kernels are primarily Greyed-Orange Group 165B-C. The kernels are viable if extracted from the endocarp and stratified shortly after harvest.

*Use.*—The subject variety, 'ROYAL ZEST FOUR', is considered to be a peach tree of mid-season maturity, which produces fruit which are firm, attractively colored, and which are useful for both local and long distance shipping.

*Keeping quality.*—Good.

*Resistance to insects and disease.*—No particular susceptibilities were noted.

*Shipping quality.*—Average. Although the new variety of peach tree possesses the described characteristics when grown under the ecological conditions prevailing in the medium chill zone of Texas it will be understood that variations of the usual magnitude and characteristics incident to the changes in growing conditions, fertilization, pruning, and pest control are to be expected.

REFERENCES

Anon. 2001 R.H.S. Colour Chart. The Royal Hort. Soc., London.

Brooks, R. M. 1958. Double Delight, Earligold, and June Gold peaches. Fruit Var. J. 3:22, U.S. Plant Pat. No. 1,884.

Brooks, R. M. and H. P. Olmo. 1997. Register of New Frail and Nut Varieties. 3rd Edition. American Society of Horticultural Science Press, Alexandria, Va.

Byrne, D. H. and T. A. Bacon. 1991. 'TexRoyal', a medium chilling peach. HortScience 26(10):1338-1340.

Byrne, D. H. and T. A. Bacon. 2004. 'TexKing', an early ripening medium chill peach. HortScience 39: 442-443. U.S. Plant Pat. No. 14,627. Mar. 23, 2004.

Byrne, D. H. and T. A. Bacon. 2004. 'Texprince', a mid season, medium chill peach. HortScience 39(3):631-632. U.S. Plant Pat. No. 14,629. Mar. 23, 2004.

Okie, W. R. 1993. 'Goldprince' and 'Scarletpearl' peaches. HortScience 28:231.

Okie, W. R. 1998. Handbook of peach and nectarine varieties. USDA, ARS, Agric. Handbook No. 714.

Rouse. R. and W. Sherman. 1989. 'TropicBeauty': a low-chilling peach for subtropical climates. HortScience 24:165-166.

Sherman, W. B. and P. M. Lyrene. 1992. Flordaprince peach. Fruit Var. J. 46:66-67.

Zaiger, C. F., G. N. Zaiger, L. M. Gardner, and G. G. Zaiger. 1990. Peach tree 'Rich Lady', U.S. Plant Pat. No. 7,290. Aug. 7, 1990.

We claim:

1. A new and distinct *Prunus persica* tree, substantially as illustrated and described herein.

* * * * *